United States Patent [19]

Swedberg

[11] Patent Number: 5,006,313

[45] Date of Patent: Apr. 9, 1991

[54] HALOGENATED SURFACE WITH REDUCED PROTEIN INTERACTION

[75] Inventor: Sally A. Swedberg, Santa Cruz, Calif.

[73] Assignee: Hewlett-Packard Company, Palo Alto, Calif.

[21] Appl. No.: 474,716

[22] PCT Filed: Jun. 2, 1988

[86] PCT No.: PCT/US88/01877

§ 371 Date: Apr. 2, 1990

§ 102(e) Date: Apr. 2, 1990

[87] PCT Pub. No.: WO89/12225

PCT Pub. Date: Dec. 14, 1989

[51] Int. Cl.⁵ ............................................. G01N 30/00
[52] U.S. Cl. ...................................... 422/70; 436/161; 204/182.2; 204/182.3; 204/183.3; 204/299 R; 210/748; 210/753

[58] Field of Search ............... 204/182.8, 182.2, 183.3, 204/299 R; 422/70; 436/161; 210/748, 753

[56] References Cited

PUBLICATIONS

"Capillary Zone Electrophoresis", Jorgenson et al., 22, *Science* (1983).

*Primary Examiner*—Robert J. Warden
*Assistant Examiner*—Laura E. Collins

[57] ABSTRACT

A method for treating a solid surface exposable to protein solutes is provided that reduces interactions of the protein solutes with the surface. Thus, a small bore capillary tube, useful for electrophoretic separation, comprises a reduced interaction phase coated along the bore that includes a terminal moiety covalently bound in the reduced interaction phase through at least one heteroatom. This terminal moiety includes a plurality of halogen atoms, and preferably is an aryl pentafluoro.

4 Claims, 1 Drawing Sheet

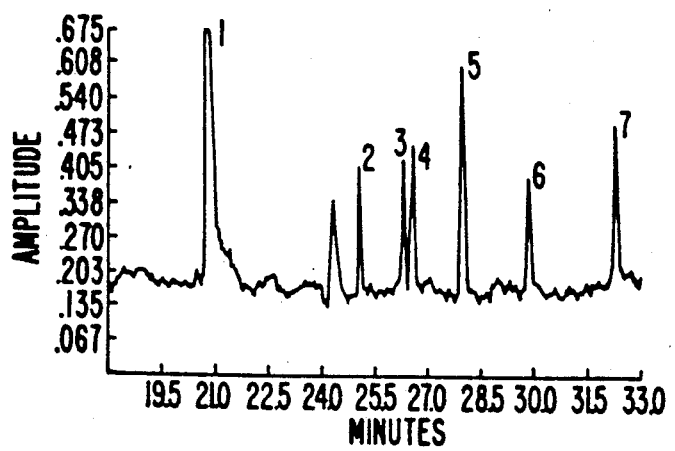
FIG._1.
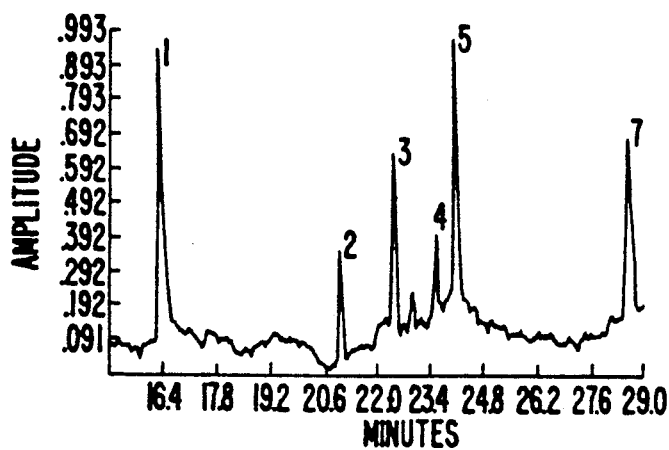
FIG._2.
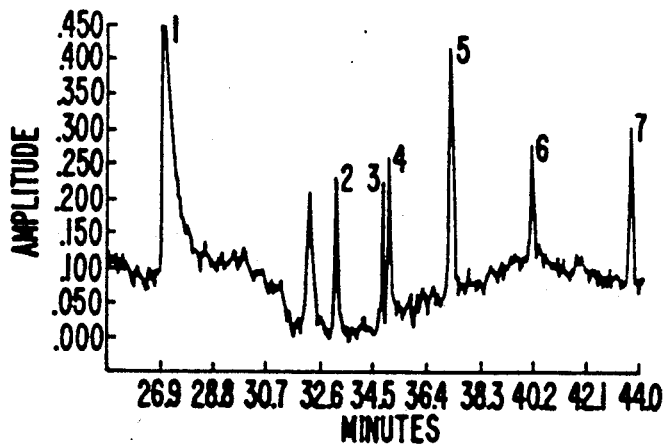
FIG._3
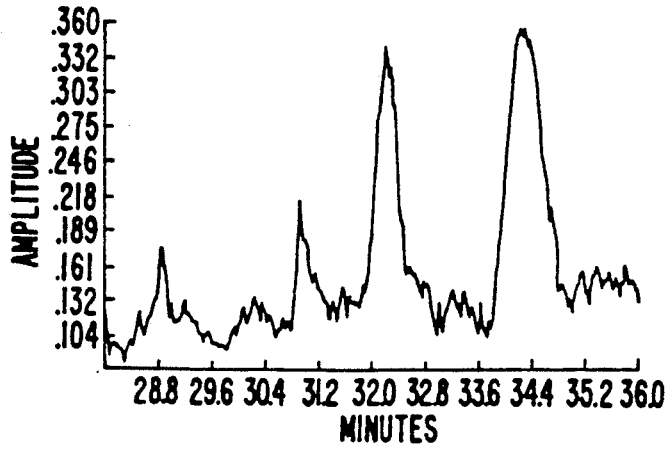
FIG._4.
(PRIOR ART)

HALOGENATED SURFACE WITH REDUCED PROTEIN INTERACTION

FIELD OF THE INVENTION

The present invention generally relates to solid surfaces exposed to protein solutes, and particularly to capillaries used in electrophoretic separations by capillary zone electrophoresis.

BACKGROUND OF THE INVENTION

Capillary zone electrophoresis ("CZE") in small capillaries (less than or equal to 75μ) was first demonstrated by Jorgenson and Lukacs, and has proven useful as an efficient method for the separation of small solutes. *J. Chromatog.*, 218 (1981), page 209; *Anal. Chem.*, 53 (1981), page 1298. The separation process relies upon an electroosmosis effect generally described as the flow of a liquid in contact with a solid surface under the influence of a tangentially applied electric field. Attractive factors for electrophoretic separations by capillary zone electrophoresis are the small sample sizes, little or no sample pretreatment, and the potential for quantification and recovery of biologically active samples.

For example, U.S. Pat. No. 4,675,300, inventors Zare et al., issued June 23, 1987 describes theories and equipment for electrokinetic separation processes employing a laser-excited fluorescence detector. The system described by Zare et al. includes a fused silica capillary with a 75μ inside diameter.

Unfortunately, one of the single greatest disadvantages of capillary zone electrophoresis lies when attempts are made to separate macromolecules such as proteins. Separations of macromolecules by CZE leads to untoward interactions of the biopolymers with the silica capillary wall.

Jorgensen et al. had noted that separation of model proteins, such as cytochrome, lysozyme and ribonuclease A, in untreated fused silica capillaries with a phosphate buffer at pH 7 was accompanied by strong tailing, and suggested this might be caused by Coulombic interactions of the positively charged proteins and the negatively charged capillary wall. Jorgensen et al., *Science*, 222 (1983) page 266.

Lauer et al., *Analytical Chemistry*, 58 (1986), page 166, has reported that the Coulombic repulsion between proteins and the capillary wall of silica capillaries can overcome adsorption tendencies of the proteins with the capillary wall. They demonstrated separations of model proteins (ranging in molecular weight from 13,000 to 77,000) by varying the solution pH relative to the isoelectric point (pI) of the proteins to change their net charge. However, disadvantages of this approach are that silica begins to dissolve above pH 7, which shortens column life and degrades performance, only proteins with pI's less than the buffer pH can be analyzed, which drastically reduces the range of useful analysis, and interactions which are not Coulombic may still occur even with proteins bearing a net negative charge due to the complexity of protein composition and structure.

Another approach to the problem of biopolymer, or protein, interactions has been to increase ionic strength. It has been demonstrated that this concept works in principle, but heating is also increased as ionic strength is increased. This heating tends to degrade the efficiency of separation.

Yet another approach to the problem of undesirable protein interactions with the capillary wall has been to coat the electrophoresis tube with a mono-molecular layer of non-crosslinked polymer. Thus, U.S. Pat. No. 4,680,201, inventor Hjerten, issued July 14, 1987 describes a method for preparing a thin-wall, narrow-bore capillary tube for electrophoretic separations by use of a bifunctional compound in which one group reacts specifically with the glass wall and the other with a monomer taking part in a polymerization process. This procedure results in a polymer coating, such as polyacrylamide coating, and is suggested for use in coating other polymers, such as poly(vinyl alcohol) and poly(vinylpyrrolidone). However, this method and capillary tube treatment tends to destroy the electroosmotic flow, and efficiencies are still rather low. These rather low efficiencies suggest that undesirable protein-wall interactions are still occurring.

SUMMARY OF THE INVENTION

It is an object of the present invention to provide small bore capillary tubes that are useful for electrophoretic separations of solutes including macromolecules, since interactions between the solutes and the bore are reduced considerably and with high efficiencies.

It is another object of the present invention to provide a method for treating a solid surface intended for exposure to protein solutes in order to reduce interactions of the solutes with the surface.

Further objects and advantages of the invention will become apparent to those skilled in the art upon examination of the specification and appended claims, as well as in practice of the present invention.

In one aspect of the present invention, a small bore capillary tube, useful for electrophoretic separations of protein solutes, comprises a reduced interaction phase coated along the bore that includes a terminal moiety covalently bound in the reduced interaction phase through at least one heteroatom of an intermediate linkage. This terminal moiety includes a plurality of halogen atoms.

In another aspect of the present invention, a method for treating a solid surface exposable to protein solutes to reduce interactions therewith comprises modifying the surface by bonding at least one molecular layer to the surface and contacting the molecular layer with an aryl halogen compound to form an outer molecular layer with halogen moieties covalently bound therein.

Capillary tubes as described by the present invention have been prepared and used in highly efficient separations for various protein mixtures with good reproducibility and consistent performance upon repeated use.

BRIEF DESCRIPTION OF THE DRAWINGS

FIGS. 1 and 3 illustrate electropherograms of a protein mixture on two columns of the invention and FIG. 2 of another protein mixture on a third inventive column; and FIG. 4 illustrates an electropherogram of the same protein mixture as in FIGS. 1 and 3, but using an unmodified (prior art) capillary tube.

DETAILED DESCRIPTION OF THE PREFERRED EMBODIMENTS

The present invention provides a solid surface that is modified so as to have reduced interactions with protein solutes. One particularly preferred application is for small bore capillary tubes, such as the tubes used in capillary zone electrophoresis. These tubes are usually less than 500μ, more typically about 20μ to about 200μ, in internal diameter. Other applications include medical uses, such as heart-lung machines and implants, where surfaces are exposed to protein solutes. For convenience, reference will hereinafter be to a small bore (less than about 500 microns) capillary tube with the bore having been modified in accordance with the invention.

The modification is whereby a reduced interaction phase is coated along the bore, or inside wall, as an interfacial layer between the inside wall of the capillary and the protein solutions when in use. The reduced interaction phase of such coating is effective to reduce interactions between protein solutes and the bore, preferably while permitting reasonably high electroosmotic flow and resultingq in excellent efficiencies. When this interfacial layer is about four to about six molecular layers thick, then it has been found that electroosmotic flow is reasonably high in use for capillary zone electrophoresis; however, fewer molecular layers (so long as at least one) or greater molecular layers are possible, and may be desirable for particular applications. When bulk molecular layers are coated on the surface, the electroosmotic flow tends to substantially decrease, which is normally not desired in a system with a single detector with species which migrate towards two electrodes.

The reduced interaction phase includes a terminal moiety that is covalently bound through at least one heteroatom. The terminal moiety is distal to the surface and covalently bound to the surface by an intermediate linkage including the heteroatom(s). The terminal moiety must include a plurality of halogen atoms, which may be substituents on an aryl group, an alkylaryl group or an alkyl group. Preferably, the terminal moiety is an aryl pentahalo.

Illustrative terminal moieties with halogen atoms substituted on an alkyl group are $CX_3-(CX_2)_n-$ where n is 0 to about 5 and X is selected from hydrogen and halogen with at least two being halogen.

Illustrative terminal moieties with halogen atoms substituted on an alkyl aryl are

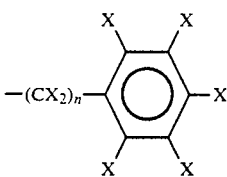

where n is 1 to about 5 and X is selected from hydrogen and halogen with at least two being halogen.

Illustrative terminal moieties substituted on an aryl group are

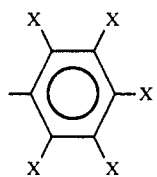

where X is selected from hydrogen and halogen with at least two being halogen.

These terminal moieties are covalently bound to the surface through at least one heteroatom of an intermediate linkage. The heteroatom is nitrogen, preferably of an amino group, oxygen, preferably of a carbonyl group, and may also include sulfur. As will be hereinafter more fully described, several heteroatoms may be present and several are preferred. The heteroatoms increase the hydrophilic character of the reduced interaction phase and, together with the halogen atoms of the terminal moieties, reduce protein interactions with the capillary tube such as caused by van der Waals' forces, hydrogen bonding and point charges. As will be hereinafter illustrated by formulas illustrating simplified models of the inventive reduced interaction phase, the surface includes silanol sites at which the coatings are bonded. These silanol sites include an oxygen molecule between the bulk surface and silicon atoms. The heteroatoms of the invention are in addition to such oxygen molecules. Thus, the intermediate linkages of which the necessary heteroatoms are a part may be viewed as being between the silicon atoms and the terminal moieties.

Particularly preferred linkages including the heteroatoms and being intermediate the surface and the terminal moieties are amides, esters, secondary amines, carbamates, carbonates and dithiols including activated carbonyls. Some illustrative intermediate linkages are:

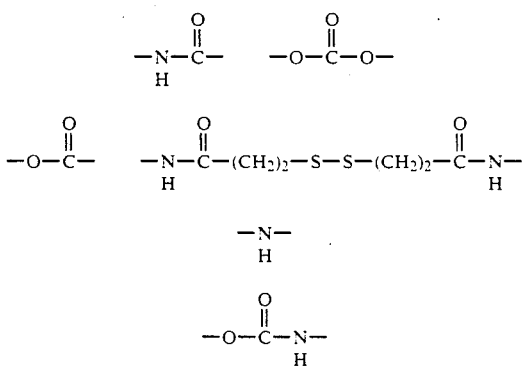

The reduced interaction phase can be obtained with or without an intermediary leash step. Surface modifications without an intermediary leash step will now be described.

SURFACE MODIFICATIONS WITHOUT LEASH

When the surface to be modified is silica based, it is first hydrated and then treated with an organo- or chloro-silane having two functional end groups. The one functional group reacts specifically with the glass wall (when the surface is of fused silica or the like). Thus, one or two alkoxy groups (such as methoxy, acetoxy, methoxyethoxy or chloro) react with the silanol groups in the wall to form a stable, covalently bonded linkage. Concentrations of silylating reagent in aqueous solution from about 0.1 wt. % to about 1 wt. % result in about four to six molecular layers being bonded to the surface. These about four to six layers are preferred to ensure there are no remaining unreacted silanol groups but still to permit a substantial electroosmotic flow. The other functional group of the silylating reagent is a nitrogen nucleophile, an oxygen nucleophile or a carbon electrophile.

The modified surface with nitrogen nucleophile, oxygen nucleophile or carbon electrophile is then reacted with the compound having halogen substituents. This halogen compound includes an electrophilic species, when the surface has nitrogen or oxygen nucleophiles, and includes a nucleophilic species, when the surface has carbon electrophiles. Exemplary reagents for the former situation are pentafluorobenzoyl chloride, pentafluorobenzaldehyde, and pentafluorobenzoic acid. An exemplary reagent for the later situation is a 2,3,4,5,6 pentafluoroalkylamine having the structure

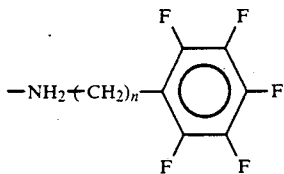

where n is 1 to about 5. When n=1, then the 2,3,4,5,6 pentafluorobenzylamine may be prepared by reduction of the nitrile. However, these electrophilic or nucleophilic halogen compounds may be selected from a wide variety of different compounds. As some further examples are:
2,3,4,5,6-pentafluorobenzhydrol,
Pentaflorobenzonitrile,
2,3,4,5,6-pentafluorobenzyl alcohol,
2,3,4,5,6-pentafluorocinnamic acid,
2,3,4,5,6-pentafluorophenoxyacetic acid,
2,3,4,5,6-pentafluorophenylacetic acid,
DL-1-(pentafluorophenyl)ethanol,
Pentafluorophenylhydrazine,
2,2,3,3,3-pentafluoro-1-propanol,
Pentafluoropropionic acid,
Pentafluoropropionic anhydride,
Pentafluoropyridine,
2,3,4,5,6-pentafluorostyrene,
Pentafluorothiophenol, and
α-Bromo-2,3,4,5,6-pentafluorotoluene.

Exemplary silylating reagents are 3-aminopropyl trimethoxysilane and 3-aminopropyl triethoxysilane. The 3-amino group is reactive with activated carboxyl-carbonyls, such as acid halide, anhydride, carbodiimide activated carbonyl or activated ester (such as N-hydroxy succinimide ester), intrinsically reactive carbonyl (e.g., aldehyde), haloalkyl carbon electrophile (such as α-halocarbonyls and haloepoxypropanes), or bisoxiranes. For example, the 3-amino group of these exemplary reagents may be reacted with pentafluorobenzoyl chloride or pentafluorobenzaldehyde to form a reduced interaction phase in accordance with the invention having the respective structures illustrated by Formulas I and II (shown as simplified models at a single silanol site where R indicates continuation of the silane polymer).

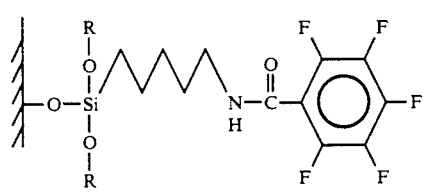

FORMULA I

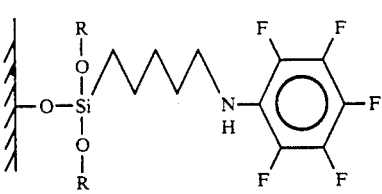

FORMULA II

Other suitable silylating reagents for surfaces desired to have nitrogen nucleophiles include:
4-aminobutyldimethylmethoxysilane,
4-aminobutyltriethoxysilane,
(aminoethylaminomethyl)phenethyltrimethosysilane,
n-(2-aminoethyl)-3-aminopropylmethyldimethoxysilane,
n-(2-aminoethyl-3-aminopropyl)trimethoxysilane,
n-2-aminoethyl-3-aminopropyltris(2-ethylhexoxy)silane,
6-(aminohexylaminopropyl)trimethoxysilane,
aminomethyltrimethylsilane,
p-aminophenyltrimethoxysilane,
aminophenyltrimethoxysilane,
3-(1-aminopropoxy)-3,3-dimethyl-1-propenyltrimethoxysilane,
3-aminopropyltris(methoxyethoxyethoxy)silane,
3-aminopropyldimethylethoxysilane,
3-aminopropylmethyldiethoxysilane,
3-aminopropyltris(trimethylsiloxy)silane, and
ω-aminoundecyltrimethoxysilane.

Silylating reagents yielding oxygen nucleophiles include:
3-glycidoxypropyldimehtylethoxysilane,
(3-glycidoxypropyl)methyldiethoxysilane,
3-glycidoxypropylmethyl-di-isopropenoxysilane, and
(3-glycidoxypropyl)trimethoxysilane.

Reaction of oxygen nucleophiles with an activated carboxyl carbonyl, such as an acid chloride or anhydride, results in a reduced interaction phase illustrated by Formula III (again, the reaction being shown as a model reaction at a single silanol site and is following reaction of the oxygen nucleophile in diol phase with a reagent such as pentafluorobenzoyl chloride or pentafluorobenzoic anhydride).

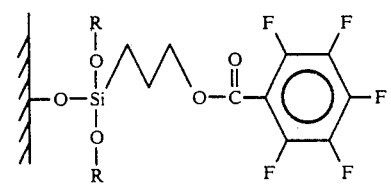

FORMULA III

Where the surface is modified to have a carbon electrophile, then the halogen compound will include a nucleophilic species, typically a nitrogen nucleophile. For example, the surface may be modified by contacting with (3-glycidoxypropyl)trimethoxysilane. The terminal oxirane may be directly reacted with 2,3,4,5,6 pentafluorobenzylamine, or may be hydrolyzed and then converted to an activated electrophilic carbon site with a reagent, such as carbonyl diimidazole, or disuccinimidyl reagent such as N,N'-disuccinimidyl-oxalate or carbonate, or the carbon site may be activated with an adjacent good leaving group, such as an organic sulfonyl halide. The activated carbonyl or activated carbon site then may be treated with the nucleophilic aryl halogen compound.

The structures illustrating use of (3-glycidoxypropyl)trimethoxysilane as a carbon electrophile followed by reaction with 2,3,4,5,6 pentafluorobenzylamine (using either the oxirane or after conversion to an oxirane, to an activated carbonyl or to a carbon site activated with an adjacent good leaving group) are illustrated by Formulas IV-V.

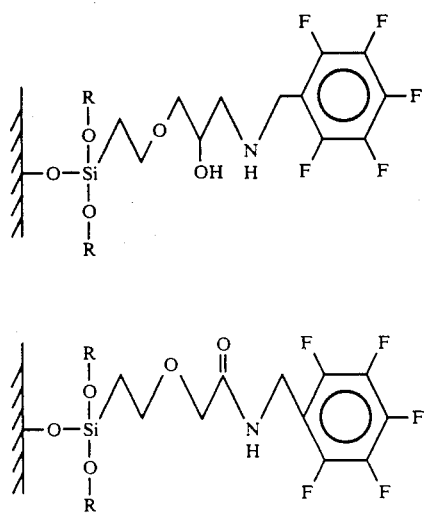

FORMULA IV

FORMULA V

SURFACE MODIFICATION WITH LEASH

Rather than reacting the surface modified nitrogen or oxygen nucleophile or carbon electrophile immediately with the desired halogen compound, an intermediary leash step may be performed to attach a spacer arm, or leash. This leash is thus part of the intermediate linkage. An advantage of such a leash step is that additional heteroatoms can be incorporated into the reduced interaction phase.

Appropriate spacer arms for reaction with the nitrogen nucleophile are electrophiles, such as activated carbonyl (e.g., acid halide, anhydride or carbodiimide activated carbonyl or activated ester (such as N-hydroxy succinimide ester), intrinsically reactive carbonyl (e.g., aldehyde), haloalkyl carbon electrophile (e.g., α-haloacetic acid or haloepoxypropanes) and with bisoxiranes. Exemplary activated carboxyl carbonyls are succinyl chloride, succinic anhydride, 1,6-hexanoic acid and carbodiimide such as EDAC(1-ethyl-3-(3-dimethylaminopropyl)-carbodiimide) or dicyclohexyl carbodiimide, and disuccinimidyl tartarate and dithio bis(succinimidyl propionate). Exemplary aldehydes are glutaraldehyde and succinic semialdehyde. Exemplary haloalkyl carbon electrophiles are α-bromoacetic acid and epichlorhydrin. Exemplary bisoxiranes are ethylene glycol diglycidyl ether and 1,4 butanediol biglycidyl ether.

A particular advantage of a dithiol leash (illustrated by the exemplary reagent dithiobis (succinimidyl propionate) is that a reduced interaction phase having such dithiol heteroatoms permits regeneration of the surface by reduction and reformation under mild conditions. Reaction Scheme 1 illustrates the preparation of such a regenerable surface.

REACTION SCHEME I

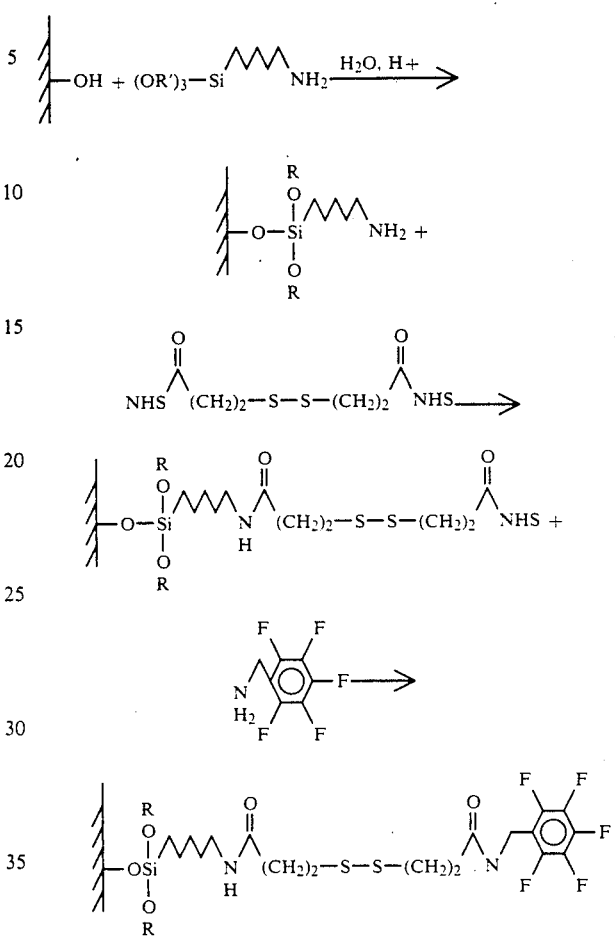

where NHS is N-hydroxy succinimide ester and R' is methyl or ethyl.

Where the surface has been modified with an oxygen nucleophile (as earlier described), then an intermediary leash step may be performed with spacer arms reacting as carbon electrophiles, such as activated carboxyl carbonyls, α-halo alkyl or epoxide carbon electrophiles. Exemplary activated carboxyl carbonyls are succinyl chloride, succinic anhydride, 1,6-hexanoic acid and carbodiimide (such as EDAC or dicyclohexyl carbodiimide), N-hydroxysuccinimide activated carbonyls (e.g., disuccinimidyl tartarate and dithiobis(succinimidyl propionate)). The latter provides a dithiol leash permitting a regenerable surface as earlier described. Exemplary halo alkyls are α-halocarbonyl (e.g., α-bromoacetic acid) and halo epoxy propanes (e.g, epibromhydrin and epichlorhydrin). Exemplary epoxides are bisoxiranes such as ethylene glycol diglycidyl ether and 1,4-butanediol diglycidyl ether.

Where the surface has been modified with a carbon electrophile, then an intermediary leash step may be used where spacers acting as nucleophiles are selected Exemplary nucleophilic reagents are diamines, carboxylic acid amines and dithiols.

Coatings of the invention have resulted in protein separations with efficiencies in the range of 300,000 to about 1,000,000 statistical moments. These highly efficient separations have been accomplished with very low protein to wall interactions (k'), usually less than 0.02. The electroosmotic flow rates at these very low k' values are believed to be about optimum for maximum efficiencies. The narrow peak widths of FIGS. 1-3 indicate such high efficiencies.

EXPERIMENTAL

The following examples, methods, materials and results are described for purposes of illustrating the present invention. However, other aspects, advantages and modifications within the scope of the invention will be apparent to those skilled in the art to which the invention pertains.

Example I illustrates the simultaneous preparation of three capillary tubes in accordance with the invention without a leash step. Example II (and FIGS. 1-3) illustrate the use of these three capillary tubes. Example III illustrates typical efficiencies that are achievable in capillary tubing of the invention. Example IV illustrates preparation of an inventive capillary tube with a leash step. Example V illustrates the effect on electroosmotic flow with different amounts of silyation (multilayer and bulk).

EXAMPLE I

Silica capillary tubing (Polymicro Technologies) of 20μ I.D. was cut into 100 cm lengths. Three such capillary tubes were then simultaneously prepared by coating a four to six molecular layered reduced interaction phase terminating in halogen moieties along the bore, or inner wall, as follows:

The silica capillary was was first hydrated with 0.1N KOH by pumping through the capillaries at a rate of about 1-2 μl/minute. The wash was continued for an 8-10 hour period. The capillaries were then washed for 2-3 hours with DI water.

The walls were then reacted with 3-aminopropyl-trimethoxysilane (3-APTS). A 1% solution of 3-APTS was prepared and adjusted to pH 3.5 with acetic acid. This solution was pumped through the capillaries at a rate of 1-2 μl/minute for one hour in one direction, then the ends were reversed and the reagent was pumped in the opposite direction for another hour. The capillaries were then attached to a manifold connected to a helium tank, and were cured overnight with a flowing stream of helium.

The capillaries were flushed with anhydrous methanol and anhydrous toluene sequentially at flow rates of 1-2μl/minute for 1-2 hours. Meanwhile, since the acyl chloride (pentafluorobenzoyl choride) is moisture sensitive, it was removed via syringe using techniques suitable for air sensitve compounds.

A 0.2M solution of the acyl chloride in anhydrous toluene was passed through the capillaries at flow rates of 1-2 μl/minute for 2-3 hours.

Following reaction, the columns were washed first with toluene, then methanol and then with DI water at flow rates of 1-2μliters/min for 1-2 hours each wash. The columns were then equilibrated to the starting buffer and were ready for use.

Formula I illustrates the composition of the reduced interaction phase formed by the just described procedure.

EXAMPLE II

Protein mixtures were made in the range of 2 mg/ml solutions in the running buffer. The running buffer was made from high purity salts, with a 200 mM phosphate buffer and 100 mM potassium chloride. The proteins used were purchased as lyophilized powders (Sigma Chemical Company). Dimethyl sulfoxide (DMSO) was used as a neutral marker.

The apparatus used was a Hippotronics power supply and an Isco detector. Detection was accomplished by using an HP 3455 A digital volt meter in conjunction with an HP Yectra computer.

All injections were made hydrodynamically by creating a low pressure at the elution end of the column. Pressure difference required and duration of injection were determined using Poiseulle's equation. Typical injection time for a 20μcapillary with a pressure difference of 20 cm of mercury was 4-5 seconds, resulting in sample volumes of 0.4 to 0.5 nl. All runs were done at 250 v/cm.

FIGS. 1-3 show electropherograms for the three inventive columns prepared as described by Example I. The unnumbered peak in FIG. 1 and FIG. 3 is the DMSO marker. There was no marker injected in the FIG. 2 separation. The FIG. 3 data was taken from a run in which the injection point was 20 cm. farther from the detection point than for FIGS. 1 and 2. In none of the FIGS. 1-4 separations was temperature controlled, which is believed to have caused the time variations. However, the protein separations of FIGS. 1-3 can be seen to be quite consistent, and with high efficiencies. FIG. 4 shows an electropherogram for a bare (untreated) silica column of the same size as the three inventive columns and run using the same conditions. A comparison of the FIG. 4 electropherogram with the FIGS. 1-3 electropherograms demonstrates the excellent resolution of the seven protein constituents by capillary tubes of the invention in contrast to the untreated capillary tube. The protein solutes resolved in FIGS. 1 and 3 were as follows (where numbered peaks correspond with the numbered proteins):

1. Lysozyme
2. Ribonuclease
3. Trypsinogen
4. Whale Myoglobin
5. Horse Myoglobin
6. Human Carbonic Anhydrase-B
7. Bovine Carbonic Anhydrase-B The protein mixture used for the FIG. 2 electropherogram included the above proteins except for human carbonic anhydrase-B.

EXAMPLE III

Typical efficiencies for the protein solutes electrophoretically separated as described by Example I on the inventive capillaries are illustrated by the data of Table 1. These efficiencies are calculated by theoretical plates according to the technique described by Kucera et al., J. Chrom., 19 (1965) p. 237.

TABLE I

| PROTEINS | pI | ELUTION TIME (MIN.) | EFFICIENCY (BY MOMENTS) |
|---|---|---|---|
| 1. Lysozyme | 11.0 | 26.8 | 325,494 |
| 2. Ribonuclease | 9.6 | 34.3 | 501,583 |
| 3. Trypsinogen | 9.3 | 37.4 | 466,374 |
| 4. Whale Myoglobin | 8.0 | 38.0 | 499,422 |
| 5. Horse Myoglobin | 7.4 | 40.6 | 512,825 |
| 6. Human Carbonic Anhydrase-B | 6.6 | 43.7 | 379,485 |
| 7. Bovine Carbonic Anhydrase-B | 5.9 | 48.5 | 482,493 |

EXAMPLE IV 0.2% glycidoxypropyltrimethoxysilane in 50 ml water was brought to a pH of 3.5 with acetic acid and allowed to polymerize for 10-15 minutes. Six 105 cm lengths of silica capillary (30 microns I.D.) were treated by passing 0.1N KOH (500 microliters) through, then washed (500 microliters) with deionized water. The silylating reagent was allowed to pass ½ hour through each end at 1-2 column volumes per minute. The coating was then cured by passing dry He through the tubes overnight.

110 microliters of tresyl in 5.0 mL of anhydrous toluene (0.2M) were transferred using syringe technique and then 250 microliters was passed through the columns. The columns had been dried first with methanol and then with anhydrous toluene (each pumped through the capillaries at 250 microliters) before treating with the tresyl reagent. The tresyl reagent was flowed at 1-2 column volumes per minute. The capillary ends were then sealed and the capillaries allowed to stand at room temperature for 1 hour. Toluene was then passed through the columns to wash away excess tresyl, again with a flow of 1-2 column volumes per minute.

88 mg of putrescine (1,4 diaminobutane) were dissolved in 5.0 mL toluene (0.2M). 250 microliters of reagent were pumped through the tresyl activated columns. The columns were allowed to sit for one hour. Toluene (250 microliters) was passed through the columns to wash away the excess reagent.

A 0.2M solution of the acyl chloride (pentafluorobenzoyl chloride) in anhydrous toluene was pumped through the amino-glyco phase described above (250 microliters). The columns were washed with toluene, methanol, and then water before being equilibrated to the running buffer.

Formula VI illustrates a composition of the reduced interaction phase formed by the just described procedure (assuming complete conversion of both activated sites).

FORMULA VI

EXAMPLE V

Two columns were prepared with different quantities of 3-APTS. One column was reacted with a one percent solution of 3-APTS while the other column was reacted with an eight percent solution of 3-APTS. Neither column was further reacted with the halogen compound, since only DMSO as marker was run to illustrate the effect on electroosmotic flow between a multi-layer and a bulk coating. The running buffer was 0.2M phosphate, pH 7; 150 volts/cm; detection was by UV (219 nm wavelength); injection was 5 cm Hg/3 sec. 0.5% DMSO in the running buffer was detected at 21.97 minutes with an electroosmotic flow of 0.460 (mm/sec) for the one percent column and at 133.70 minutes for an electroosmotic flow of 0.099 (mm/sec) for the eight percent column. It is believed that optimum flow rates for maximum efficiency are between about 0.5 to about 0.8 mm/sec, although the bulk coated column may be useful for other applications.

Although the present invention has been described with reference to specific examples, it should be understood that various modification and variations can be easily made by those skilled in the art without departing from the spirit of the invention. Accordingly, the foregoing disclosure should be interpreted as illustrative only and not to be interpreted in a limiting sense. The present invention is limited only by the scope of the following claims.

It is claimed:

1. A device for electrophoretic separations of protein solutes, comprising:
    a small bore capillary tube having a reduced interaction phase coated along the bore and effective to reduce interaction between protein solute and the bore, the reduced interaction phase including a terminal moiety covalently bound in the reduced interaction phase through at least one heteroatom, the at least one heteroatom forming a linkage intermediate the bore and the terminal moiety, the terminal moiety including a plurality of halogen atoms.

2. The capillary tube as in claim 1 wherein the at least one heteroatom is one or more of nitrogen, oxygen or sulfur and the at least one heteroatom increases hydrophilicity of the reduced interaction phase.

3. The capillary tube as in claim 1 wherein the terminal moiety is a plurality of halogen atoms that are substituents on an aryl group, an alkylaryl group or an alkyl group.

4. The capillary tube as in claim 1 wherein the terminal moiety is an aryl pentahalo group.